United States Patent [19]

Hagen et al.

[11] 4,395,415
[45] Jul. 26, 1983

[54] N-OXO-PYRIDIN-2-YL-DITHIO-(4-NITRO-2-TRICHLOROMETHYLBENZENE) AND A FUNGICIDAL FORMULATION CONTAINING SAME

[75] Inventors: Helmut Hagen, Frankenthal; Hans Ziegler, Mutterstadt; Celia J. Mappes, Westheim; Ernst-Heinrich Pommer, Limburgerhof, all of Fed. Rep. of Germany

[73] Assignee: BASF Aktiengesellschaft, Fed. Rep. of Germany

[21] Appl. No.: 256,128

[22] Filed: Apr. 21, 1981

[30] Foreign Application Priority Data

May 16, 1980 [DE] Fed. Rep. of Germany ....... 3018716

[51] Int. Cl.³ .................... C07D 213/71; A61K 31/44
[52] U.S. Cl. ..................................... 424/263; 546/294; 546/288; 548/137; 548/263; 560/106; 560/254; 568/21; 568/22
[58] Field of Search ................. 546/288, 294; 424/263

[56] References Cited

U.S. PATENT DOCUMENTS

4,163,020  7/1979  Hagen et al. .................... 260/454
4,261,924  4/1981  Hagen et al. .................... 564/102

FOREIGN PATENT DOCUMENTS

10616   2/1981  European Pat. Off. ........... 564/102
2721917 of 0000  Fed. Rep. of Germany ...... 260/454
2810698  9/1979  Fed. Rep. of Germany ...... 564/102

OTHER PUBLICATIONS

Hackh's Chemical Dictionary, Fourth Edition, p. 75, McGraw-Hill Pub.

Pharmacological Reviews, vol. 21, No. 4, pp. 331-336, Williams and Wilkins Pub. (1969).
Chemical Abstracts, vol. 81 (1974), No. 22237g.
Chemical Week 1972, Jun. 21, p. 46.
Chemical Week 1972, Jul. 26, p. 39.
Farm Chemicals Handbook 1976, p. D43.
Chemical Week 1972, Jul. 26, p. 22.
Chemical Week 1972, Jun. 21, p. 55.

*Primary Examiner*—Alan L. Rotman
*Attorney, Agent, or Firm*—Keil & Witherspoon

[57] ABSTRACT

4-Nitro-2-trichloromethylbenzenesulfenic acid derivatives of the formula

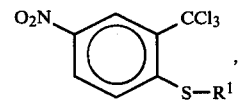

where $R^1$ is nitroimidazolyl, which is substituted by alkyl, phenyl or benzyl, or $R^1$ is S-alkyl, which is substituted by an S—S-phenyl radical, itself substituted in the phenyl moiety by nitro and trichloromethyl, or which is substituted by —O—CO—$R^2$, where $R^2$ is unsubstituted or substituted alkyl, unsubstituted or phenyl-substituted alkenyl, or unsubstituted or chlorine- or nitro-substituted phenyl, or monoalkylamino or dialkylamino, or unsubstituted or mono-chlorine-substituted or polychlorine-substituted aminophenyl, or $R^1$ is —S—$R^3$, where $R^3$ is unsubstituted or carboxyl-substituted aryl, triazolyl, unsubstituted or alkyl-substituted thiadiazolyl, unsubstituted or alkyl-, cyano- or oxo-substituted pyridyl, or unsubstituted or alkyl-, amino-, hydroxy- or oxo-substituted pyrimidinyl, and fungicides containing these compounds.

2 Claims, No Drawings

N-OXO-PYRIDIN-2-YL-DITHIO-(4-NITRO-2-TRI-CHLOROMETHYLBENZENE) AND A FUNGICIDAL FORMULATION CONTAINING SAME

The present invention relates to novel, valuable 4-nitro-2-trichloromethylbenzenesulfenic acid derivatives having a useful fungicidal action, processes for their preparation, fungicides containing these compounds, and methods of controlling fungi, using these compounds.

It is known that N-trichloromethylthiotetrahydrophthalimide (Chemical Week June 21, 1972, page 46), tetramethylthiuram disulfide (Chemical Week July 26, 1972, page 39), 2-thiocyanomethylthio-benzothiazole (Farm Chemicals Handbook 1976, page D 43), manganese ethylene-bis-dithiocarbamate (Chemical Week July 26, 1972, page 22) and 2,4,5,6-tetrachloro-isophthalodinitrile (Chemical Week June 21, 1972, page 55) can be used as fungicides. However, their action is not fully satisfactory.

It is also known that 4-nitro-2-trichloromethylphenyl disulfides (German Laid-Open Application DOS No. 2,810,698) and 4-nitro-2-trichloromethylphenyl-sulfenamides (European Patent Application No. 79/103,662) may be used as fungicides.

We have found that the 4-nitro-2-trichloromethylphenylsulfenic acid derivatives of the formula

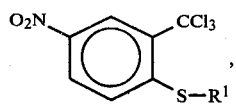

where $R^1$ is 4(5)-nitroimidazol-1-yl, which is 2-substituted by alkyl of 1 to 4 carbon atoms, phenyl or benzyl, or $R^1$ is S-alkyl of 2 to 4 carbon atoms, which is substituted by an S—S-phenyl radical, itself substituted in the phenyl moiety by nitro and trichloromethyl, or which is substituted by —O—CO—$R^2$, where $R^2$ is unsubstituted or substituted alkyl of 1 to 4 carbon atoms, unsubstituted or phenyl-substituted alkenyl of 2 to 4 carbon atoms, or unsubstituted or chlorine- or nitro-substituted phenyl, or monoalkylamino or dialkylamino of 1 to 6 carbon atoms, or unsubstituted or monochlorine-substituted or poly-chlorine-substituted aminophenyl, or $R^1$ is —S—$R^3$, where $R^3$ is unsubstituted or carboxyl-substituted aryl, triazolyl, unsubstituted or alkyl-substituted thiadiazolyl, unsubstituted or alkyl-, cyano- or oxo-substituted pyridyl, or pyrimidinyl which is unsubstituted or is monosubstituted or polysubstituted by alkyl, amino, hydroxyl or oxo, are fungicidally more effective than the conventional active ingredients.

Examples of preferred meanings are the following:
$R^1$: -S-propyl-3-dithio-(4-nitro-2-trichloromethylbenzene).

$R^3$: phenyl-2-carboxylic acid, triazol-2-yl, 5-methyl-thiadiazol-2-yl, 4,6-dimethyl-3-cyanopyridin-2-yl, pyridin-2-yl-1-oxide, 4,6-dimethylpyrimidin-2-yl, 4,6-diaminopyrimidin-2-yl, 4-hydroxypyrimidin-2-yl, 4-methylpyrimidin-2-yl and pyrimidin-2-yl.

$R^2$: aminophenyl, amino-3,4-dichlorophenyl, aminomethyl, aminoisopropyl, methyl and phenyl.

The novel compounds may be prepared, for example, by reacting 4-nitro-2-trichloromethyl-benzenesulfenyl chloride, of the formula 4, with a compound of the formula 5, where $R^1$ has the above meanings, in an inert solvent, at from $-20°$ to $150°$ C., in the presence or absence of an acid acceptor.

The reaction can be represented by the following equation:

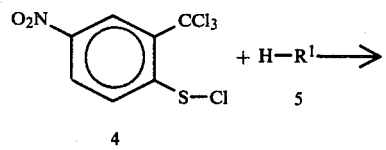

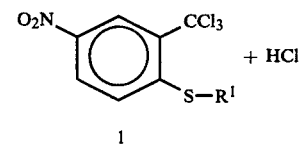

Examples of suitable inert solvents for the reaction are carboxylic acids, eg. acetic acid, saturated aliphatic and cyclic ethers, eg. diethyl ether, tetrahydrofuran and dioxane, aliphatic carboxylic acid esters, eg. ethyl acetate and butyl acetate, lower alcohols, eg. isobutanol, chlorohydrocarbons, eg. methylene chloride, and aromatic hydrocarbons, eg. benzene and toluene.

Amongst the solvents mentioned, diethyl ether, tetrahydrofuran and acetic acid are particularly preferred.

The acid acceptors can be organic or inorganic bases, such as NaOH, $Na_2CO_3$, sodium acetate, potassium acetate, triethylamine and pyridine. Sodium acetate and potassium acetate are preferred.

The preferred reaction temperature is from $0°$ to $60°$ C. Compounds which contain a basic group can also be prepared as the hydrochlorides.

The novel compounds of the formula 3 below, containing the radical —OCOR$^2$, are prepared, for example, by reacting 2-hydroxymethyl-(4-nitro-2-trichloromethylphenyl) disulfide, of the formula 6, with a carbonyl compound, which may be a carboxylic acid chloride, a carboxylic acid anhydride, a carbamic acid chloride or an isocyanate, of the formula 7, where $R^2$ has the above meanings, in an inert solvent, in the presence or absence of an equivalent amount of an acid acceptor, at from $-20°$ to $150°$ C. The reaction can be represented by the following equation:

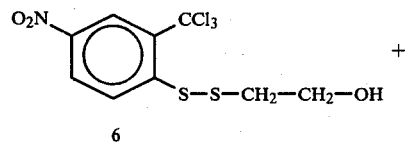

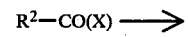

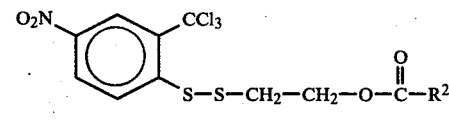

Examples of suitable inert solvents for the reaction are chlorohydrocarbons, eg. methylene chloride, saturated aliphatic and cyclic ethers, eg. diethyl ether, tetrahydrofuran and dibutyl ether, aromatic hydrocarbons, eg. benzene and toluene, or an excess of the carbonyl compound itself may be used. Where the reaction is carried out with a carboxylic acid chloride or a carbamic acid chloride, an acid acceptor is advantageously present. Suitable acid acceptors are inorganic or organic bases, such as triethylamine, pyridine, NaOH and $Na_2CO_3$.

The reaction is preferably carried out at from 0° to 150° C., depending on the reactivity of the carbonyl compound.

The novel compounds can also be prepared, for example, by reacting 4-nitro-2-trichloromethylbenzenesulfenyl chloride of the formula 4 with a mercaptan of the formula 8, where $R^2$ has the above meanings, in an inert solvent at from 20° to 150° C. The reaction may be represented by the following equation:

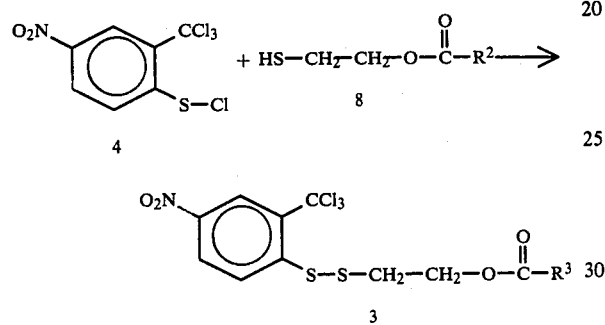

Advantageously, the preferred solvents and reaction conditions mentioned above are used.

The starting compound of the formula 4, namely 4-nitro-2-trichloromethylbenzenesulfenyl chloride, can be prepared by the process described in German Laid-Open Application DOS Nos. 2,721,917.

The starting compound 2-hydroxyethyl-(4-nitro-2-trichloromethylphenyl) disulfide is advantageously prepared by the process described in German Laid-Open Application DOS No. 2,810,698.

EXAMPLE 1

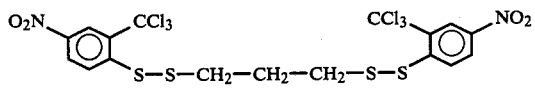

1,3-Bis-dithio-(4-nitro-2-trichloromethylphenyl)-propane 61.4 g of 4-nitro-2-trichloromethylbenzenesulfenyl chloride, dissolved in 200 ml of diethyl ether, are reacted with a solution of 10.8 g of 1,3-dimercaptopropane in 400 ml of ether at 10° C. After a reaction time of 12 hours at 20° C., the precipitate is filtered off and dried over potassium hydroxide. 51 g (78% of theory) of 1,3-bis-dithio-(4-nitro-2-trichloromethylphenyl)-propane, of melting point 97° C., are obtained.

| | Analysis | | | | |
|---|---|---|---|---|---|
| | C | H | Cl | N | S |
| calculated: | 31.4 | 1.8 | 32.8 | 4.3 | 19.7 |
| found: | 31.6 | 1.9 | 33.0 | 4.4 | 19.6 |

EXAMPLE 2

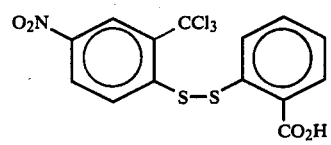

o-(4-Nitro-2-trichloromethyl-phenyldithio)-benzoic acid 61.4 g of 4-nitro-2-trichloromethylbenzenesulfenyl chloride are reacted with 32 g of 2-mercaptobenzoic acid by a method similar to that of Example 1. 74 g (87% of theory) of o-(4-nitro-2-trichloromethylphenyldithio)-benzoic acid of melting point 224° C., are obtained.

| | Analysis | | | | |
|---|---|---|---|---|---|
| | C | H | Cl | N | S |
| calculated: | 39.7 | 1.7 | 25.1 | 3.3 | 15.1 |
| found: | 40.0 | 1.8 | 25.0 | 3.2 | 15.1 |

EXAMPLE 3

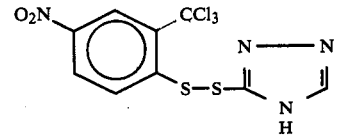

Triazol-2-yl-dithio-(4-nitro-2-trichloromethylbenzene)

30.7 g of 4-nitro-2-trichloromethylbenzenesulfenyl chloride, dissolved in 300 ml of glacial acetic acid, are reacted with 10 g of 3-mercapto-1,2,4-triazole at 20° C. After 12 hours, the precipitate is filtered off and dried over potassium hydroxide. 21 g (57% of theory) of triazol-2-yl-dithio-(4-nitro-2-trichloromethylbenzene), of melting point 189° C., are obtained.

| | Analysis | | | | |
|---|---|---|---|---|---|
| | C | H | Cl | N | S |
| calculated: | 29.1 | 1.1 | 28.7 | 15.1 | 17.2 |
| found: | 29.3 | 1.3 | 28.9 | 15.1 | 17.2 |

EXAMPLE 4

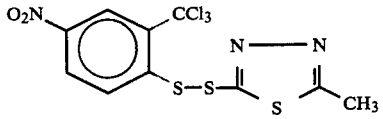

5-Methyl-thiadiazol-2-yl-dithio-(4-nitro-2-trichloromethylbenzene)

61.4 g of 4-nitro-2-trichloromethylbenzenesulfenyl chloride, dissolved in 200 ml of ether, are reacted with 26.5 g of 2-mercapto-5-methyl-1,3,4-thiadiazole, dissolved in 600 ml of ether, at 20° C. After 12 hours, the precipitate is filtered off and treated with methanol. 72 g (89% of theory) of 5-methyl-thiadiazol-2-yl-dithio-(4- nitro-2-trichloromethylbenzene), of melting point 124° C., are obtained.

|  | Analysis | | | | |
| --- | --- | --- | --- | --- | --- |
|  | C | H | Cl | N | S |
| calculated: | 29.8 | 1.5 | 26.5 | 10.4 | 23.8 |
| found: | 29.9 | 1.7 | 26.4 | 10.4 | 23.9 |

EXAMPLE 5

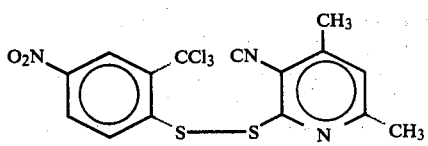

4,5-Dimethyl-3-cyano-pyridin-2-yl-dithio-(4-nitro-2-trichloromethylbenzene)

61.4 g of 4-nitro-2-trichloromethylbenzenesulfenyl chloride, dissolved in 500 ml of glacial acetic acid, are reacted with 33 g of 1,4-dimethyl-5-cyano-6-mercaptopyridine at 20° C. After 2 hours, the solution is filtered, 500 ml of water are added and the precipitate formed is filtered off, washed with 10% strength sodium carbonate solution and with ether, and dried over potassium hydroxide. 58 g (67% of theory) of 4,6-dimethyl-3-cyano-pyridin-2-yl-dithio-(4-nitro-2-trichloromethylbenzene), of melting point 132° C., are obtained.

|  | Analysis | | | | |
| --- | --- | --- | --- | --- | --- |
|  | C | H | Cl | N | S |
| calculated: | 41.4 | 2.3 | 24.5 | 9.7 | 14.7 |
| found: | 41.6 | 2.5 | 24.5 | 9.8 | 14.8 |

EXAMPLE 6

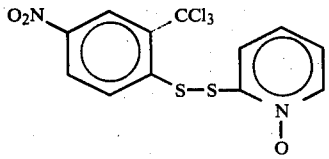

N—Oxo-pyridin-2-yl-dithio-(4-nitro-2-trichloromethylbenzene)

61.4 g of 4-nitro-2-trichloromethylbenzenesulfenyl chloride are reacted with 25.4 g of 2-mercaptopyridine-N-oxide by a method similar to that of Example 5. Water is then added and the product is filtered off and dried over potassium hydroxide and recrystallized from ether. 75 g (93% of theory) of N-oxo-pyridin-2-yl-dithio-(4-nitro-2-trichloromethylbenzene), of melting point 167° C., are obtained.

|  | Analysis | | | | |
| --- | --- | --- | --- | --- | --- |
|  | C | H | Cl | N | S |
| calculated: | 36.2 | 1.8 | 26.8 | 7.0 | 16.1 |
| found: | 36.1 | 2.0 | 27.0 | 6.9 | 16.2 |
| hydrochloride: melting point 166° C. | | | | | |

EXAMPLE 7

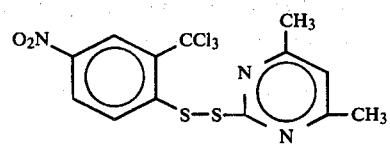

4,6-Dimethylpyrimidin-2-yl-dithio-(4-nitro-2-trichloromethylbenzene)

61.4 g of 4-nitro-2-trichloromethylbenzenesulfenyl chloride, dissolved in 500 ml of glacial acetic acid, are mixed with 28 g of 4,6-dimethyl-2-mercaptopyrimidine and 16.4 g of sodium acetate at 20° C. After 12 hours, the precipitate is filtered off, washed with water and dried over potassium hydroxide. 75 g (91% of theory) of 4,6-dimethylpyrimidin-2-yl-dithio-(4-nitro-2-trichloromethylbenzene), of melting point 151° C., are obtained.

|  | Analysis | | | | |
| --- | --- | --- | --- | --- | --- |
|  | C | H | Cl | N | S |
| found: | 38.0 | 2.4 | 25.9 | 10.2 | 15.6 |
| calculated: | 38.2 | 2.5 | 25.9 | 10.1 | 15.4 |

EXAMPLE 8

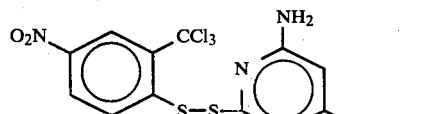

4,6-Diaminopyrimidin-2-yl-dithio-(4-nitro-2-trichloromethylbenzene) hydrochloride 61.4 g of 4-nitro-2-trichloromethylbenzenesulfenyl chloride are reacted with 28.4 g of 4,6-diamino-2-mercaptopyrimidine by a method similar to that described in Example 7. The end product was reacted with HCl. 58 g (70% of theory) of 4,5-diaminopyrimidin-2-yl-dithio-(4-nitro-2-trichloromethylbenzene) hydrochloride, of melting point 250° C., are obtained.

|  | Analysis | | | | |
| --- | --- | --- | --- | --- | --- |
|  | C | H | Cl | N | S |
| calculated: | 29.4 | 2.0 | 31.6 | 15.6 | 14.2 |
| found: | 29.8 | 2.2 | 31.4 | 15.4 | 14.0 |

EXAMPLE 9

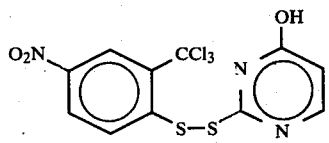

4-Hydroxy-pyrimidin-2-yl-dithio-(4-nitro-2-trichloromethylbenzene)

61.4 g of 4-nitro-2-trichloromethylbenzenesulfenyl chloride are reacted with 26.6 g of 4-hydroxy-2-mercaptopyrimidine by a method similar to that described in Example 7. Water is then added and the product is filtered off. 75 g (94% of theory) of 4-hydroxypyrimidin-2-yl-dithio-(4-nitro-2-trichloromethylbenzene), of melting point 174° C., are obtained.

|  | Analysis | | | | |
|---|---|---|---|---|---|
|  | C | H | Cl | N | S |
| calculated: | 33.1 | 1.5 | 26.7 | 10.5 | 16.0 |
| found: | 33.0 | 1.4 | 26.9 | 10.4 | 15.9 |

EXAMPLE 10

Using a similar method to Example 7, 4-methyl-2-mercaptopyrimidine gives 4-methylpyrimidin-2-yl-dithio-4-nitro-2-trichloromethylbenzene in the form of an oil.

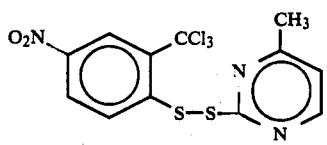

EXAMPLE 11

Using a similar method to Example 7, 2-mercaptopyrimidine gives pyrimidin-2-yl-dithio-4-nitro-2-trichloromethylbenzene

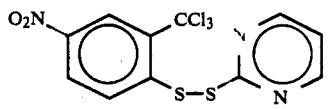

Melting point: 98°–99° C.

EXAMPLE 12

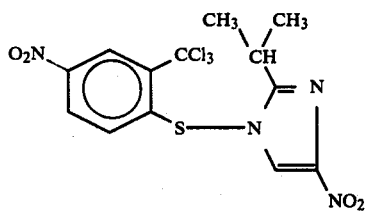

4(5)-Nitro-2-isopropylimidazol-1-yl
4-nitro-2-trichloromethylphenyl sulfide 61.4 g of 4-nitro-2-trichloromethylphenylsulfenyl chloride are reacted with 31 g of 4(5)-nitro-2-isopropylimidazole. 62 g (73% of theory) of 4(5)-nitro-2-isopropylimidazol-1-yl 4-nitro-2-trichloromethylphenyl sulfide, of melting point 181° C., are obtained.

|  | Analysis | | | | |
|---|---|---|---|---|---|
|  | C | H | Cl | N | S |
| calculated: | 36.7 | 2.6 | 25.0 | 13.2 | 7.5 |
| found: | 36.7 | 2.6 | 25.2 | 13.3 | 7.6 |

EXAMPLE 13

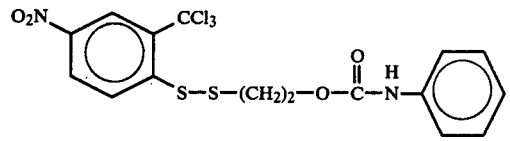

Beta-(phenylaminocarbonyloxy)-ethyl
4-nitro-2-trichloromethyl disulfide 34.9 g of beta-hydroxyethyl 4-nitro-2-trichloromethylphenyl disulfide, in 500 ml of toluene, are mixed with 10.8 ml of phenyl isocyanate. The mixture is left for 24 hours at 80° C. and the solvent is then removed under reduced pressure. 43 g, corresponding to 92% of theory, of 2-ethoxycarbonylaminophenyl 4-nitro-2-trichloromethylphenyl disulfide are obtained as a pale oil.

|  | Analysis | | | | |
|---|---|---|---|---|---|
|  | C | H | Cl | N | S |
| calculated: | 41.1 | 2.8 | 22.8 | 6.0 | 13.7 |
| found: | 41.3 | 2.9 | 22.8 | 6.0 | 13.9 |

EXAMPLE 14

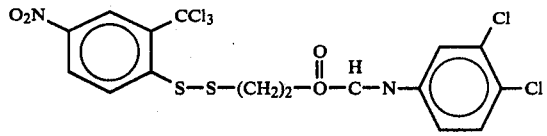

2-Ethoxycarbonylamino-(3,4-dichlorophenyl)
4-nitro-2-trichloromethylphenyl disulfide 34.9 g of 2-hydroxyethyl 4-nitro-2-trichloromethylphenyl disulfide are reacted with 18.8 g of dichlorophenyl isocyanate, using a method similar to that described in Example 13. 51 g (98% of theory) of 2-ethoxycarbonylamino-(3,4-dichlorophenyl) 4-nitro-2-trichloromethylphenyl disulfide are obtained as a pale oil.

|  | Analysis | | | | |
|---|---|---|---|---|---|
|  | C | H | Cl | N | S |
| calculated: | 36.9 | 2.1 | 34.0 | 5.4 | 12.3 |
| found: | 37.0 | 2.3 | 33.8 | 5.4 | 12.2 |

EXAMPLE 15

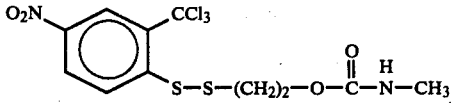

2-Ethoxycarbonylaminomethyl 4-nitro-2-
trichloromethylphenyl disulfide 52.3 g of 2-hydroxyethyl 4-nitro-2-trichloromethylphenyl disulfide are reacted, using a similar method to that described in Example 13, with 15 ml of methyl isocyanate. 60 g (98% of theory) of 2-ethoxycarbonylaminomethyl 4-nitro-2-trichloromethylphenyl disulfide, of melting point 90°–91° C., are obtained.

|  | Analysis | | | | |
| --- | --- | --- | --- | --- | --- |
|  | C | H | Cl | N | S |
| calculated: | 32.6 | 2.7 | 26.3 | 6.9 | 15.8 |
| found: | 32.8 | 2.9 | 26.1 | 7.0 | 15.6 |

EXAMPLE 16

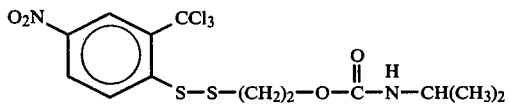

2-Ethoxycarbonylaminoisopropyl 4-nitro-2-trichloromethylphenyl disulfide 34.9 g of 2-hydroxyethyl 4-nitro-2-trichloromethylphenyl disulfide are reacted with 10 ml of isopropyl isocyanate, using a method similar to that described in Example 13. 41 g (94% of theory) of 2-ethoxycarbonylaminoisopropyl 4-nitro-2-trichloromethylphenyl disulfide are obtained as a pale oil.

|  | Analysis | | | | |
| --- | --- | --- | --- | --- | --- |
|  | C | H | Cl | N | S |
| calculated: | 36.0 | 3.5 | 24.6 | 6.5 | 14.8 |
| found: | 36.0 | 3.5 | 24.8 | 6.3 | 14.9 |

EXAMPLE 17

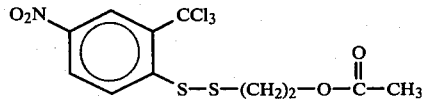

2-Ethoxyacetyl 4-nitro-2-trichloromethylphenyl disulfide 69.6 g of 2-hydroxyethyl 4-nitro-2-trichloromethylphenyl disulfide are dissolved in 200 ml of acetic anhydride at 20° C. and left to stand at this temperature for 24 hours. The excess acetic anhydride is then removed under reduced pressure and the residue is recrystallized from naphtha. 60 g (88% of theory) of 2-ethoxyacetyl 4-nitro-2-trichloromethylphenyl disulfide, of melting point 89° C., are obtained.

|  | Analysis | | | | |
| --- | --- | --- | --- | --- | --- |
|  | C | H | Cl | N | S |
| calculated: | 33.8 | 2.6 | 27.3 | 3.6 | 16.4 |
| found: | 34.0 | 2.8 | 27.4 | 3.6 | 16.3 |

EXAMPLE 18

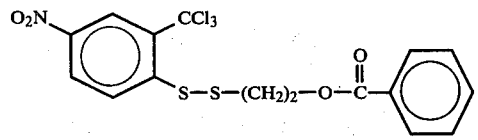

2-Ethoxybenzoyl 4-nitro-2-trichloromethylphenyl disulfide 11.7 ml of benzoyl chloride, dissolved in 200 ml of ether, are added to 34.9 g of 2-hydroxyethyl 4-nitro-2-trichloromethylphenyl disulfide, dissolved in 500 ml of ether, at 10° C. After a reaction time of 12 hours at 20° C., the solution is washed with water and evaporated down. The residue is recrystallized from methanol, giving 37 g (82% of theory) of 2-ethoxybenzoyl 4-nitro-2-trichloromethylphenyl disulfide, of melting point 79°–80° C.

|  | Analysis | | | | |
| --- | --- | --- | --- | --- | --- |
|  | C | H | Cl | N | S |
| calculated: | 42.4 | 2.7 | 23.5 | 3.1 | 14.1 |
| found: | 42.4 | 2.8 | 23.7 | 3.1 | 14.2 |

EXAMPLE 19

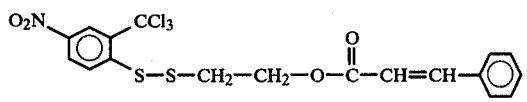

2-Ethoxycinnamyl 4-nitro-2-trichloromethylphenyl disulfide 34.9 g of 2-hydroxyethyl 4-nitro-2-trichloromethylphenyl disulfide and 10.1 g of diethylamine, in 300 ml of methylene chloride, are reacted with 16.7 g of cinnamyl chloride, dissolved in 100 ml of methylene chloride, at 20° C. After 12 hours, the solution is washed with water, dried and evaporated down under reduced pressure. 45 g, corresponding to 94% of theory, of 2-ethoxycinnamyl 4-nitro-2-trichloromethylphenyl disulfide are obtained as a pale oil.

|  | Analysis | | | | |
| --- | --- | --- | --- | --- | --- |
|  | C | H | Cl | N | S |
| calculated: | 45.1 | 2.9 | 22.3 | 2.9 | 13.4 |
| found: | 44.9 | 2.9 | 22.4 | 2.9 | 13.5 |

EXAMPLE 20

Using a similar method to that described in Example 19, crotonyl chloride gives 2-ethoxycrotonyl 4-nitro-2-trichloromethylphenyl disulfide as an oil.

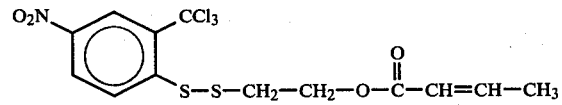

The new compounds have an excellent fungitoxic action on various kinds of injurious fungi which are of economic significance in the protection of crops and materials. They are for instance excellently suited for combating Septoria nodorum and Septoria tritici in wheat, Helminthosporium species in cereals, Pythium species in Leguminoseae and cotton, Cercospora species in groundnuts, beets, and coffee, Mycosphaerella in bananas, and Piricularia in rice. The new compounds may also be used for protecting materials. For example the following material-damaging fungi may be controlled: *Aspergillus niger, Penicillium glaucum, Chaetomium globosum, Paecilomyces variotii, Cladosporium herbarum,* and *Pullularia pullulans*. Furthermore, some of the compounds are characterized by an excellent bactericidal action, e.g., on *Staphylococcus aureus*. When the compounds are used as fungicides for protecting materials, e.g., in paints, the amount of active ingredient applied is from 0.5 to 5%, based on the total weight of the material to be preserved. The fungicidal agents contain from 0.1 to 95 wt%, and preferably from 0.5 to 90 wt%, of active ingredient. The application rates depend on the effect desired, and range from 0.001 to 3 kg and more, but preferably from 0.01 to 1 kg of active ingredient per hectare. The new active ingredients may also be used as fungicidally effective constituents of oily wood preservatives for protecting wood against wood-destroying or wood-discoloring fungi. Application is effected by treating the wood with these agents, e.g., by impregnation or painting.

The active ingredients may be applied as such, in the form of formulations thereof, or application forms prepared therefrom, e.g., as directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene of diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products or sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The active ingredients according to the invention may also be mixed and applied with other, prior art, fungicides. In many cases, the spectrum of fungicidal action is increased; with a number of these fungicidal compositions, synergistic effects also occur; i.e., the fungicidal action of the combination product is greater than the effect of the individual components added together.

Examples of fungicides which may be combined with the active ingredients according to the invention are as follows:
ferric dimethyldithiocarbamate
zinc dimethyldithiocarbamate
manganese ethylenebisdithiocarbamate
zinc ethylenebisthiocarbamate
tetramethylthiuram disulfide
3,5-dimethyl-1,3,5-2H-tetrahydrothiadiazine-2-thione
manganese-zinc ethylenediamine-bisdithiocarbamate
zinc-(N,N'-propylene-bisdithiocarbamate)
ammonia complex of zinc-(N,N'-ethylene)-bisdithiocarbamate and
N,N'-polyethylene-bis-(thiocarbamoyl)-disulfide
ammonia complex of zinc-(N,N'-propylene-bisdithiocarbamate) and
N,N'-polypropylene-bis-(thiocarbamoyl)-disulfide
dinitro-(1-methylheptyl)-phenylcrotonate
2-sec-butyl-4,6-dinitrophenyl-3,5-dimethylacrylate
2-sec-butyl-4,6-dinitrophenylisopropylcarbonate
2,4,5-trichlorophenol
pentachlorophenol
barium salt of pentachlorophenol
pentachlorophenyl acetate
pentachlorobenzyl alcohol
di-(5-chloro-2-hydroxyphenyl)-methane
phenyl-(5-chloro-2-hydroxyphenyl)-methane
N-trichloromethylthiotetrahydrophthalimide
N-trichloromethylthiophthalimide
N-fluorodichloromethylthiophthalimide
N-(1,1,2,2-tetrachloroethylthio)-tetrahydrophthalimide
2-heptadecyl-2-imidazoline acetate
2,4-dichloro-6-(o-chloroanilino)-s-triazine
diethylphthalimidophosphorothionate
5-amino-1-[bis-(dimethylamino)-phosphynyl]-3-phenyl-1,2,4-triazole
5-ethoxy-3-trichloromethyl-1,2,4-thiadiazole
2,3-dicyano-1,4-dithiaanthraquinone
quinoxaline-2,3-cycl.-trithiocarbonate methyl 1-(butylcarbamoyl)-2-benzimidazole carbamate
2-methoxycarbonylaminobenzimidazole
2-thiocyanomethylthiobenzothiazole
4-(2-chlorophenylhydrazono)-3-methyl-5-isooxazolone
1-(1,2,4-triazolyl-1')-[4'-chlorophenoxy)]-3,3-dimethyl-butan-2-one
1-(1-imidazoyl)-2-allyloxy-2-(2,4-dichlorophenyl)-ethane
2-(O,O-diethylthionophosphoryl)-5-methyl-6-carbethoxypyrazolo-(1,5a)-pyrimidine
pyridine-2-thiol-1-oxide
8-hydroxyquinoline and its copper salt
5,5-dimethyl-3-(3,5-dichlorophenyl)-2,4-dioxo-1,3-oxazolidine
5-methyl-5-vinyl-3-(3,5-dichlorophenyl)-2,4-dioxo-1,3-oxazolidine
2-[furyl-(2)]-benzimidazole
piperazine-1,4-diyl-bis[1-(2,2,2-trichloroethyl)-formamide]
2-[thiazolyl-(4)]-benzimidazole
5-butyl-2-dimethylamino-4-hydroxy-6-methylpyrimidine
bis-(p-chlorophenyl)-3-pyridinemethanol
1,2-bis-(3-ethoxycarbonyl-2-thioureido)-benzene
1,2-bis-(3-methoxycarbonyl)-2-thioureido)-benzene
dodecylguanidine acetate
3-[2-(3,5-dimethyl-2-oxycyclohexyl)-2-hydroxyethyl]-glutarimide hexachlorobenzene
N-dichlorofluoromethylthio-N,N'-dimethyl-N-phenyl-sulfuric acid diamide
N-dichlorofluoromethylthio-N-methyl-N'-methyl-N-phenylsulfuric acid diamide
2,4,5,6-tetrachloroisophthalonitrile
1-(3,4-dichloroanilino)-1-formylamino-2,2,2-trichloroethane,
2,6-dimethyl-N-tridecylmorpholine and its salts
2,6-dimethyl-N-cyclododecylmorpholine and its salts
2,3-dichloro-1,4-naphthoquinone
1,4-dichloro-2,5-dimethoxybenzene
p-dimethylaminobenzene diazosodium sulfonate
1-chloro-2-nitropropane
polychloronitrobenzenes such as pentachloronitrobenzene
methyl isocyanate
triphenyl tin acetate
fungicidal antibiotics, e.g., griseofulvin and kasugamycin
mercaptobenzothiazole
methyl-N-(2,6-dimethylphenyl)-N-(2-furoyl)-alaminate
methyl-N-(2,6-dimethylphenyl)-N-(2-methoxyacetyl)-alaminate
2-cyano-N-[(ethylamino)-carbonyl]-2-(methoximino)-acetamide
β-(4-chlorphenxy)-(1,1-dimethyl)-1H-1,2,4-triazole-1-ethanol
benzisothiazolone
tetrafluorodichloroacetone
1-phenylthiosemicarbazide
aluminum complex of N'-hydroxy-N-cyclohexyl-diazenium oxide
Bordeaux mixture
nickel-containing compounds, and sulfur.

These agents may be added to the fungicides according to the invention in a weight ratio of from 1:10 to 10:1. They may also be added immediately before use (tankmix).

EXAMPLE I 10 parts by weight of compound 2 is dissolved in a mixture consisting of 90 parts by weight of xylene, 6 parts by weight of the adduct of 8 to 10 moles of ethylene oxide with 1 mole of oleic acid-N-monoethanolamide, 2 parts by weight of the calcium salt of dodecylbenzenesulfonic acid, and 2 parts by weight of the adduct of 40 moles of ethylene oxide with 1 mole of castor oil. By pouring the solution into water and uniformly distributing it therein, an aqueous dispersion is obtained.

EXAMPLE II 20 parts by weight of compound 3 is dissolved in a mixture consisting of 640 parts by weight of cyclohexanone, 30 parts by weight of isobutanol, 5 parts by weight of the adduct of 7 moles of ethylene oxide with 1 mole of isooctylphenol, and 5 parts by weight of the adduct of 40 moles of ethylene oxide with 1 mole of castor oil. By pouring the solution into water and finely distributing it therein, an aqueous dispersion is obtained.

EXAMPLE III 20 parts by weight of compound 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into water and uniformly distributing it therein, an aqueous dispersion is obtained.

EXAMPLE IV 80 parts by weight of compound 3 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 70 parts by weight of powdered silica gel, and triturated in a hammer mill. By uniformly distributing the mixture in water, a spray liquor is obtained.

EXAMPLE V 3 parts by weight of compound 3 is intimately mixed with 97 parts by weight of particulate kaolin. A dust is obtained containing 3% by weight of the active ingredient.

EXAMPLE VI 30 parts by weight of compound 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE VII 40 parts by weight of compound 1 is intimately mixed with 10 parts of the sodium salt of a phenolsulfonic acid-urea-formaldehyde condensate, 2 parts of silica gel and 48 parts of water to give a stable, aqueous dispersion. Dilution in water gives an aqueous dispersion.

EXAMPLE VIII 20 parts of compound 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The following prior art compounds were employed for comparison purposes in the experiments described below:

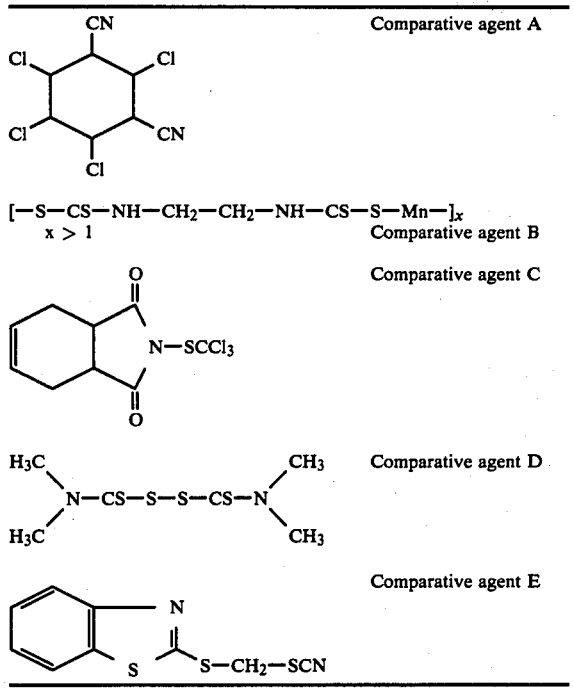

Action of *Septoria nodorum* in Wheat

Leaves of pot-grown wheat plants of the "Jubilar" variety are sprayed to runoff with aqueous spray liquors containing 0.05 and 0.1 wt.% of active ingredient in emulsified form. After the sprayed-on layer has dried, the plants are sprayed with a spray suspension of the fungus *Septoria nodorum* and placed at 16° to 18° C. in a high-humidity chamber to obtain optimum conditions for fungus growth. After 14 days, the disease has developed on the untreated control plants to such an extent that the leaf blotches cover the major portion of the leaves.

The results show that new active ingredients 1, 2, 3, 4, 5, 6, 7, 8, 9, 10, 11, 12, 13, 14, 15, 16, 17, 19 and 20 have a better fungicidal action than comparative agent A.

Action on *Helminthosporium sativum* in Wheat

Leaves of pot-grown wheat plants of the "Jubilar" variety are sprayed to runoff with aqueous spray liquors containing 0.05 and 0.1 wt.% of active ingredient in emulsified form. After the sprayed-on layer has dried, the first leaves are cut off and placed, leaf underside up, on glass rods in large glass dishes (13 cm in diameter). To keep the leaves fresh, the cuts are dipped in water which contains 0.005% of benzimidazole. The leaves (6 per treatment) are sprayed with a spore suspension of the fungus *Helminthosporium sativum*. Glass lids are then placed on the dishes, which are then kept at room temperature (20° C.) After 6 days, the disease has developed on the untreated control plants to such an extent that the leaf blotches cover the major portion of the leaves.

The results show that new active ingredients 1, 2, 4, 11, 12, 17 and 18 have a better fungicidal action than prior art comparative agent D.

Fungicidal action on *Aspergillus niger*

The active ingredients are added to a nutrient solution ideally suited for promoting the growth of the fungus *Aspergillus niger*, in amounts of 100, 50, 25 and 10 parts by weight per million parts of nutrient solution. 20 ml lots of the nutrient solution treated in this manner are placed in 100 ml glass flasks and inoculated with 0.3 mg of Aspergillus spores. The flasks are incubated at 36° C. for 120 hours, and the extent of fungus spread—predominantly on the surface of the nutrient solutions—is then assessed.

The results show that new active ingredients 3, 6 and 12 have a better fungicidal action than prior art comparative agents B, C, D and E, than active ingredients 2, 5 and 10 of Example 26 of German Laid-Open Application DE-OS No. 2,810,698; and than active ingredients 2, 9 and 12 of Example 51 of European Patent Application No. 79 103 662.

Fungicidal Action on Emergence Diseases in Peas 100 g samples of pea seeds of the "Senator" variety are carefully shaken for about 5 minutes in glass bottles with 300 mg (=0.3 wt%) of seed disinfectant formulations containing (dry basis) 40% of active ingredient. Subsequently, 3×10 seeds are sown 3 cm deep in pots in a compost naturally and heavily infested with the fungi Pythium spec., Aphanomyces spec. and *Fusarium oxysporum*. The boxes are set up in the greenhouse at from 17° to 20° C. The number of healthy pea plants is determined after 21 days.

The results show that new active ingredients 10, 11, 13 and 16 have a better fungicidal action than prior art comparative agent C.

We claim:
1. N-Oxo-pyridin-2-yl-dithio-(4-nitro-2-trichloromethylbenzene).
2. A fungicidal formulation comprising a carrier and/or diluent and from 0.1 to 95 weight percent of the compound of claim 1.

* * * * *